United States Patent
Nagel et al.

(10) Patent No.: US 10,238,796 B2
(45) Date of Patent: Mar. 26, 2019

(54) LINEAR ACTOR ARRANGEMENT

(71) Applicant: Sanofi-Aventis Deutschland GmbH, Frankfurt am Main (DE)

(72) Inventors: Thomas Nagel, Tharandt (DE); Rene Richter, Tharandt (DE); Robert Witt, Dredsen (DE); Richard Guenther, Dredsen (DE); Peter Raab, Rostock (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 259 days.

(21) Appl. No.: 14/405,434

(22) PCT Filed: Jun. 25, 2013

(86) PCT No.: PCT/EP2013/063236
§ 371 (c)(1),
(2) Date: Dec. 4, 2014

(87) PCT Pub. No.: WO2014/001309
PCT Pub. Date: Jan. 3, 2014

(65) Prior Publication Data
US 2015/0151046 A1    Jun. 4, 2015

(30) Foreign Application Priority Data

Jun. 27, 2012 (EP) .................................... 12173960

(51) Int. Cl.
*A61M 5/145* (2006.01)
*F16H 31/00* (2006.01)
(Continued)

(52) U.S. Cl.
CPC ...... *A61M 5/14546* (2013.01); *A61M 5/1452* (2013.01); *F16H 31/007* (2013.01);
(Continued)

(58) Field of Classification Search
CPC .... A61M 5/14546; A61M 2005/14506; A61M 5/1452; A61M 2205/0266
(Continued)

(56) References Cited

U.S. PATENT DOCUMENTS 533,575 A    2/1895   Wilkens
5,226,895 A  7/1993   Harris
(Continued)

FOREIGN PATENT DOCUMENTS

EP    0937471 A2    8/1999
EP    0937476 A2    8/1999
(Continued)

OTHER PUBLICATIONS

Japanese Office Action for JP Application No. 2015-519049, dated Feb. 7, 2017.
(Continued)

*Primary Examiner* — Edelmira Bosques
(74) *Attorney, Agent, or Firm* — Fish & Richardson P.C.

(57) ABSTRACT

The invention relates to a linear actor arrangement, comprising a linear actor with two ends whose distance is variable depending on an energizing of the linear actor, wherein each end is attached to a respective first or second coupling element which engage a coupling surface, wherein the coupling surface and the coupling elements exhibit mating surface structures in such a manner that the coupling elements are prevented from moving in a direction while being allowed to move in an opposite direction.

14 Claims, 1 Drawing Sheet

Amended

(51) Int. Cl.
  *H02K 41/03* (2006.01)
  *H02N 2/02* (2006.01)
(52) U.S. Cl.
  CPC .............. *H02K 41/03* (2013.01); *H02N 2/023*
    (2013.01); *A61M 2005/14506* (2013.01);
    *A61M 2205/0266* (2013.01); *A61M 2205/0272*
    (2013.01); *A61M 2205/0294* (2013.01); *A61M*
    *2207/00* (2013.01); *Y10T 74/1856* (2015.01);
    *Y10T 83/04* (2015.04); *Y10T 409/303752*
    (2015.01)
(58) Field of Classification Search
  USPC ........................................................ 604/154
  See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,476,224 B2* | 1/2009 | Petrakis | G01K 1/02 |
| | | | 222/54 |
| 2001/0016710 A1 | 8/2001 | Nason et al. | |
| 2002/0052578 A1 | 5/2002 | Moller | |
| 2002/0120235 A1 | 8/2002 | Enggaard | |
| 2003/0050609 A1 | 3/2003 | Sams | |
| 2003/0229310 A1* | 12/2003 | Flaherty | A61M 5/1452 |
| | | | 604/151 |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0041085 A1 | 2/2009 | Petrakis | |
| 2009/0187151 A1* | 7/2009 | Kleyman | A61B 17/00491 |
| | | | 604/224 |
| 2009/0275916 A1 | 11/2009 | Harms et al. | |

FOREIGN PATENT DOCUMENTS

| | | |
|---|---|---|
| JP | 2011-515176 A | 5/2011 |
| WO | 9938554 A1 | 8/1999 |
| WO | 9948546 A1 | 9/1999 |
| WO | 0110484 A1 | 2/2001 |
| WO | 2004009995 A1 | 1/2004 |
| WO | 2009118553 A1 | 10/2009 |
| WO | 2009136209 A1 | 11/2009 |
| WO | 2012/028498 A1 | 3/2012 |

OTHER PUBLICATIONS

International Preliminary Report on Patentability and Written Opinion in Application No. PCT/EP2013/063236, dated Dec. 31, 2014, 6 pages.
International Search Report in Application No. PCT/EP2013/063236, dated Oct. 25, 2013, 4 pages.

* cited by examiner

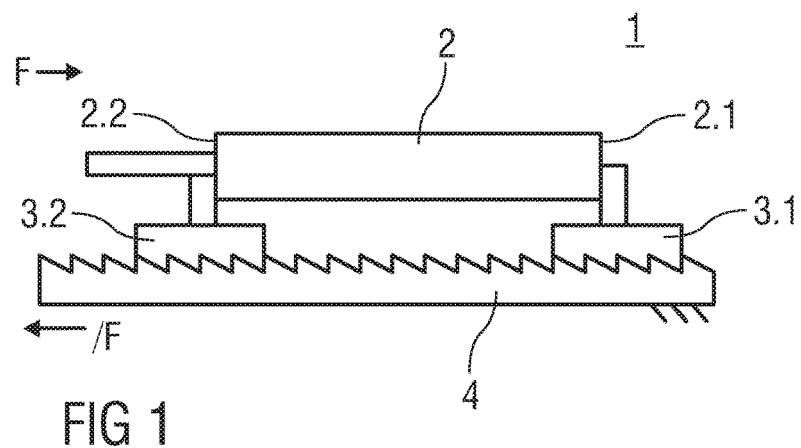
FIG 1
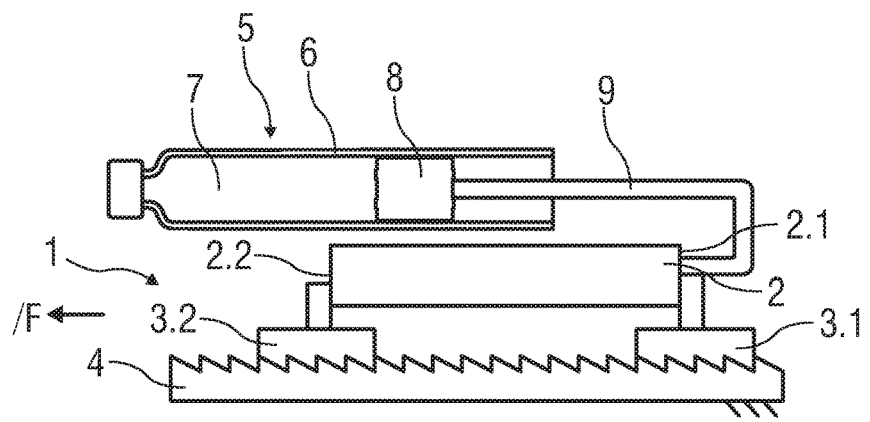
FIG 2
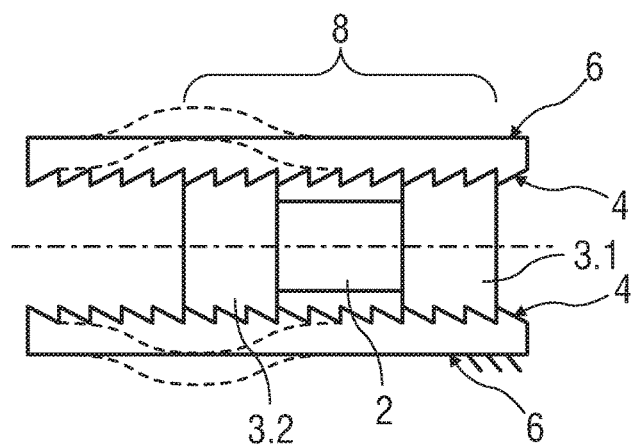
Amended FIG 3

LINEAR ACTOR ARRANGEMENT

CROSS REFERENCE TO RELATED APPLICATIONS

The present application is a U.S. National Phase Application pursuant to 35 U.S.C. § 371 of International Application No. PCT/EP2013/063236 filed Jun. 25, 2013, which claims priority to European Patent Application No. 12173960.1 filed Jun. 27, 2012. The entire disclosure contents of these applications are herewith incorporated by reference into the present application.

FIELD OF INVENTION

The invention relates to a linear actor arrangement.

BACKGROUND

Conventional drug delivery devices comprise a container defining a cavity within for retaining a drug. A nozzle, e.g. an injection needle, is arranged at a distal end of the drug delivery device, wherein the nozzle is in fluid communication with the cavity in the container. A stopper with a plunger is disposed in the container for displacing the drug.

US 2001/0016710 A1 discloses a drive mechanism for a medication delivery device including a force receiving member, a force applying member and a shape memory alloy actuator. The force applying member is operatively coupled to the force receiving member to move the force receiving member to a different position relative to the force applying member. The shape memory alloy actuator is formed from a shape memory alloy material and is operatively coupled to the force applying member. The shape memory alloy actuator is heat activated to distort the shape memory actuator from a first shape to a second shape to activate the force applying member to act upon the force receiving member to move the force receiving member to a different position relative to the force applying member.; Also, the shape memory alloy actuator is returned to the first shape from the second shape after the force receiving member is moved to a different position relative to the force applying member. In addition, the shape memory alloy actuator may be activated by applying and removing an electrical current to the shape memory element. For example, the drive mechanism may further include a power source coupled to the shape memory actuator to provide the electric current to the shape memory actuator. In addition, the shape memory actuator may be formed from Nitinol material, such as a wire.

SUMMARY

It is an object of the present invention to provide an improved means suitable for moving the stopper within the container of a drug delivery device.

The object is achieved by a linear actor arrangement according to claim 1.

Preferred embodiments of the invention are given in the dependent claims.

According to the invention a linear actor arrangement comprises a linear actor with two ends whose distance is variable depending on an energizing of the linear actor, wherein each end is attached to a respective first or second coupling element which engage a coupling surface, wherein the coupling surface and the coupling elements exhibit mating surface structures in such a manner that the coupling elements is prevented from moving in a direction while being allowed to move in an opposite direction.

Conventional art linear actors usually have either large adjustment ranges with low actoric force and precision or high actoric force and precision with small adjustment ranges. The latter group, e.g. piezo actors or solenoids, may be operated with very high frequencies.

When combined with the coupling elements operatively engaging the coupling surface the linear actor arrangement may achieve greater overall adjustment ranges by summing up a great number of the relatively small single oscillations of the linear actor and channel them in the opposite direction. The coupling elements operatively engaging the coupling surface prevent the linear actor from oscillating in the same place by controlling its gliding behaviour with respect to the coupling surface.

For example, the coupling surface and the coupling elements may have a saw tooth structure. Thus, movement in one direction is prevented by an engagement of a vertical edge of a saw tooth of the coupling element with the vertical edge of an opposite saw tooth of the coupling surface. A sliding movement in the opposite direction is however possible. The sliding movement can be reversed only if the movement is smaller than a distance of one saw tooth, and the coupling element slides back in the first position. If the distance of movement is larger than one saw tooth, a movement of a coupling element in the first direction is prevented by an engagement of a saw tooth of the coupling element with the next opposite saw tooth of the coupling surface.

The saw tooth structure comprises structures in which the slopes of the tooth like edges have a different angle, for example one long rising slope with a small angle and a short falling slope with a bigger angle. Such an asymmetric pattern results in different forces required to move a coupling element (with a corresponding surface) in opposite directions perpendicular to the pattern.

If the linear actor is controlled to expand, e.g. by applying a voltage, the first coupling element remains engaged to the coupling surface while the second coupling element is pushed in the opposite direction by one tooth's or a few teeth's distance, depending on the oscillation amplitude of the linear actor. If the voltage controlling the linear actuator is switched off or reversed, the linear actuator contracts, the second coupling element, which has just been advanced in the opposite direction locks to the coupling surface while the first coupling element is pulled in the opposite direction in such a manner that the whole linear actor moves in the opposite direction a distance in the order of the actor expansion.

The surface structure may be a micro saw tooth structure, wherein the linear actor has an adjustment range which is greater than a distance between adjacent teeth of the saw tooth structure.

The linear actor may have an adjustment range which is greater than a multiple of the distance between adjacent teeth of the saw tooth structure.

The saw tooth structure may be generated by one of the methods milling, laser-structuring, wet chemical anisotropic etching, eroding or scoring with a high precision saw such as a wafer saw. The saw tooth structure may likewise be achieved by moulding using a mould processed with one of the aforementioned methods. The mould may also be manufactured by stamping with a stamp, sintering with a master, LIGA (German acronym for Lithographie, Galvanoformung, Abformung—Lithography, Electroplating, and Molding) or laser sintering.

The linear actor arrangement may be applied in a drug delivery device comprising a container defining a cavity for a drug, wherein a stopper is disposed within the cavity for being axially translated so as to displace the drug from the cavity, wherein the linear actor is arranged for driving the stopper. The linear actor arrangement is likewise suited for other applications, where high precision adjustments are desired, such as linear stages or multi axis stages, lifting systems or other positioning systems. In order to allow adjustment in two mutually opposite directions two linear actor arrangements may be arranged in antiparallel, wherein for each direction one of the linear actor arrangements may be respectively engaged while the other is de-coupled and vice versa for the other direction.

Propelling the stopper by the linear actor arrangement according to the invention allows for drug delivery devices with a reduced total length, as a plunger handle is not required.

Typically the container and the stopper have a cylindrical cross section. However, different cross sections, such as prismatic, rectangular, square or elliptical or likewise are possible.

In an exemplary embodiment, a plunger may be arranged between the linear actor and the stopper.

In an exemplary embodiment, the stopper has a micro saw tooth structure so as to serve as the second coupling element, wherein the linear actor is arranged between the stopper and first coupling element, wherein an inside of the wall of the container has a micro saw tooth structure and serves as the coupling surface for both coupling elements.

The coupling elements or the coupling surface or a part of the coupling surface or at least one of the saw tooth structures may be resilient in order to compensate the fluctuations of the diameter when moving over the saw tooth edges. The resilience may be achieved by materials structured by moulding.

Employing high force and high precision linear actors with an intrinsic low adjustment range and accordingly structured surfaces allows for achieving high overall adjustment ranges while maintaining the advantage of high force and high precision.

High adjustment speed may be achieved by controlling the linear actor 2 with an appropriately high frequency. For example, the frequency may be in the range of a few Hz up to a few kHz. In exemplary embodiments the tooth distance may be 20 μm, 40 μm or 80 μm. Other tooth distances, in particular greater tooth distances are likewise possible.

The linear actor arrangement allows for maintaining the linear actor, the coupling elements and hence the stopper in a locked in position without having to apply a holding current.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a schematic longitudinal section of a linear actor arrangement,

FIG. 2 is a schematic longitudinal section of the linear actor arrangement with a drug delivery device, and FIG. 3 is a schematic longitudinal section of the linear actor arrangement integrated into a drug delivery device.

Corresponding parts are marked with the same reference symbols in all figures.

DETAILED DESCRIPTION

FIG. 1 is a schematic longitudinal section of a linear actor arrangement 1. The linear actor arrangement 1 comprises a linear actor 2 arranged to expand or to contract when respectively energized, e.g. by applying a voltage, so that a distance between two ends 2.1, 2.2 of the actor may be varied. Each end 2.1, 2.2 is attached to a respective first or second coupling element 3.1, 3.2 which operatively engages a coupling surface 4. The coupling surface 4 and the coupling elements 3.1, 3.2 exhibit mating surface structures, e.g. a micro saw tooth structure in such a manner that the coupling element 3.1, 3.2, when engaged to the coupling surface 4 is prevented from moving in a direction F while being allowed to move in an opposite direction/F.

The linear actor 2 may be arranged as a piezo actor or a solenoid with a relatively high actoric force and precision but a relatively small adjustment range. Such a linear actor 2 may be operated with very high frequencies.

When combined with the described coupling elements 3.1, 3.2 operatively engaging the coupling surface 4, the linear actor arrangement 1 may achieve greater overall adjustment ranges by summing up a great number of the relatively small single oscillations of the linear actor 2 and channel them in the direction/F. The coupling elements 3.1, 3.2 operatively engaging the coupling surface 4 prevent the linear actor 2 from oscillating in the same place by controlling its gliding behaviour with respect to the coupling surface 4.

Referring to the embodiment illustrated in FIG. 1, if the linear actor 1 is controlled to expand, e.g. by applying a voltage, the first coupling element 3.1 remains engaged to the coupling surface 4 while the second coupling element 3.2 is pushed in the direction/F by one tooth's or a few teeth's distance, depending on the oscillation amplitude of the linear actor 2. If the voltage controlling the linear actuator 2 is switched off or reversed, the linear actuator 2 contracts, the second coupling element 3.2, which has just been advanced in the direction/F locks to the coupling surface 4 while the first coupling element 3.1 is pulled in the direction/F in such a manner that the linear actor 2 moves in the direction/F a distance in the order of the actor expansion, which may be a multiple of the tooth distance.

If the linear actor 2 is a piezo actor, which expands and contracts by just a few micrometers the tooth distance of the saw tooth profile has to be appropriately small.

The saw tooth structure may be generated by one of the methods milling, laser-structuring, wet chemical anisotropic etching, eroding or scoring with a high precision saw such as a wafer saw. The saw tooth structure may likewise be achieved by moulding using a mould processed with one of the aforementioned methods. The mould may also be manufactured by stamping with a stamp, sintering with a master, LIGA (German acronym for Lithographie, Galvanoformung, Abformung—Lithography, Electroplating, and Molding) or laser sintering.

The coupling surface 4 may be completely or partially furnished with the saw tooth structure. The saw tooth structure may be restricted to sections of the coupling surface 4 which are intended as travelling distance for the linear actuator 2. The number of engaging teeth of the coupling elements 3.1, 3.2 determines a maximum force which the linear actor 2 can apply to a load acting in the direction F.

FIG. 2 is a schematic longitudinal section of the linear actor arrangement 1 with a drug delivery device 5. The drug delivery device 5 comprises a cylindrical container 6 defining a cavity 7 for a drug within. A stopper 8 is disposed within the cavity 7 for being axially translated so as to displace the drug from the cavity 7 through a nozzle, such as an injection needle or a jet nozzle. A plunger 9 is arranged between the linear actor 2 and the stopper 8 so that the stopper 8 may be operated by the linear actor 2 in the above described manner. While the container 6 is held in place, the plunger 9 is pushed by linear actor arrangement 1. Each tooth step that the coupling element 3.1 is moved in the direction/F, the bung or stopper 8 is moved by an equivalent distance within the cylindrical container 6 and expels a given volume of the drug or medicament through the nozzle.

FIG. 3 is a schematic longitudinal section of the linear actor arrangement 1 integrated into a drug delivery device 5. The linear actor 2 is arranged between the stopper 8, which has a micro saw tooth surface so as to serve as the second coupling element 3.2, and a similar first coupling element 3.1. The inside of the container 6 wall also has a micro saw tooth surface and serves as the coupling surface 4 for both coupling elements 3.1, 3.2. In order to allow the coupling elements 3.1, 3.2 to move within the container 6 either the container 6 wall or a part of it or the coupling elements 3.1, 3.2 may be designed to be sufficiently resilient to compensate the fluctuations of the diameter when moving over the saw tooth edges. The resilience may be achieved by materials structured by moulding. In the embodiment of FIG. 3 the resilience of the wall of the container 6 is exaggeratedly illustrated for clarity.

Employing high force and high precision linear actors 2 with an intrinsic low adjustment range and accordingly structured surfaces allows for achieving high overall adjustment ranges while maintaining the advantage of high force and high precision.

Employing piezo actors allows for step widths which are significantly smaller than the distance of the saw teeth by applying and holding a fraction of the voltage required for adjusting the distance of the saw teeth.

High adjustment speed may be achieved by controlling the linear actor 2 with an appropriately high frequency.

The linear actor arrangement 1 allows for maintaining the linear actor 2, the coupling elements 3.1, 3.2 and hence the stopper 8 in a locked in position without having to apply a holding current.

The drug delivery device 5 may be applied for delivering liquid drugs such as proteins, vaccines, complex carbohydrates or growth hormones.

The linear actor 2 may be a high precision and high force linear actor with a small adjustment range as the total adjustment range may be partitioned into an arbitrary number of small steps by the described arrangement of the linear actor 2 and the coupling elements 3.1, 3.2 and coupling surface 4.

The invention claimed is:

1. A linear actor arrangement, comprising:
 a coupling surface; and
 a linear actor comprising a first end and a second end,
 wherein a distance between the first end and the second end of the linear actor is variable depending on an energizing of the linear actor,
 wherein the first end and the second end of the linear actor are respectively attached directly to first and second coupling elements that engage the coupling surface in a manner such that the first and second coupling elements are spaced apart from each other during expansion and contraction of the linear actor according to the energizing of the linear actor,
 wherein the coupling surface and the first and second coupling elements comprise complementary mating surface structures that prevent the first and second coupling elements from moving in a first direction while allowing the first and second coupling elements to move in a second direction, the second direction opposite to the first direction,
 wherein each complementary mating surface structure is a micro saw tooth structure comprising a plurality of teeth, and
 wherein the linear actor has an adjustment range that is greater than a distance between two consecutive teeth of the plurality of teeth of the saw tooth structure.

2. Linear actor arrangement according to claim 1, characterized in that the linear actor is a piezo actor.

3. Linear actor arrangement according to claim 1, characterized in that the linear actor is a solenoid.

4. Linear actor arrangement according to claim 1, characterized in that the saw tooth structure is generated by milling.

5. Linear actor arrangement according to claim 1, characterized in that the saw tooth structure is generated by laser-structuring.

6. Linear actor arrangement according to claim 1, characterized in that the saw tooth structure is generated by wet chemical anisotropic etching.

7. Linear actor arrangement according to claim 1, characterized in that the saw tooth structure is generated by eroding.

8. Linear actor arrangement according to claim 1, characterized in that the saw tooth structure is generated by scoring with a high precision saw.

9. Linear actor arrangement according to claim 1, characterized in that the saw tooth structure is generated by moulding using a mould processed with one of the methods milling, laser-structuring, wet chemical anisotropic etching, eroding, scoring with a high precision saw, stamping, sintering, LIGA or laser sintering.

10. A drug delivery device, comprising:
 a cylindrical container defining a cavity for a drug,
 wherein a stopper is disposed within the cavity for being axially translated so as to displace the drug from the cavity, and
 wherein the linear actor according to claim 1 is arranged for driving the stopper.

11. Drug delivery device according to claim 10, characterized in that a plunger is arranged between the linear actor and the stopper.

12. Drug delivery device according to claim 10, characterized in that the stopper has the micro saw tooth structure so as to serve as the second coupling element, wherein the linear actor is arranged between the stopper and first coupling element, wherein an inside of the wall of the cylindrical container has the micro saw tooth structure and serves as the coupling surface for both coupling elements.

13. Drug delivery device according to claim 12, characterized in that the coupling elements or the coupling surface or a part of the coupling surface or at least one of the saw tooth structures is resilient.

14. A linear actor arrangement, comprising:
 a coupling surface; and
 a linear actor comprising a first end and a second end,
 wherein a distance between the first end and the second end of the linear actor is variable depending on an energizing of the linear actor,
 wherein the first end and the second end of the linear actor are respectively attached directly to first and second coupling elements that engage the coupling surface in a manner such that the first and second coupling elements are spaced apart from each other during expansion and contraction of the linear actor according to the energizing of the linear actor,
 wherein the coupling surface and the first and second coupling elements comprise complementary mating surface structures that prevent the first and second coupling elements from moving in a first direction while allowing the first and second coupling elements to move in a second direction, the second direction opposite to the first direction, wherein each complementary mating surface structure is a micro saw tooth structure comprising a plurality of teeth, wherein the linear actor has an adjustment range that is greater than a distance between two consecutive teeth of the plurality of teeth of the saw tooth structure, wherein the linear actor is a piezo actor or a solenoid, and wherein the distance between the two consecutive teeth is in a range of 20 μm to 80 μm.

* * * * *

UNITED STATES PATENT AND TRADEMARK OFFICE
CERTIFICATE OF CORRECTION

PATENT NO. : 10,238,796 B2  
APPLICATION NO. : 14/405434  
DATED : March 26, 2019  
INVENTOR(S) : Thomas Nagel et al.

Page 1 of 1

It is certified that error appears in the above-identified patent and that said Letters Patent is hereby corrected as shown below:

On the Title Page

Column 1 (Inventors), Line 3, delete "Dredsen," and insert -- Dresden, --

Column 1 (Inventors), Line 4, delete "Dredsen," and insert -- Dresden, --

Signed and Sealed this
Thirtieth Day of July, 2019

Andrei Iancu
*Director of the United States Patent and Trademark Office*